US009385463B2

(12) United States Patent
Sakakibara et al.

(10) Patent No.: US 9,385,463 B2
(45) Date of Patent: Jul. 5, 2016

(54) CONTACT MEMBER AND MANUFACTURING METHOD OF SENSOR

(71) Applicant: NGK INSULATORS, LTD., Nagoya-shi, Aichi (JP)

(72) Inventors: Kazuhito Sakakibara, Toyota (JP); Koichi Masuda, Nagoya (JP); Kenji Isaka, Nagoya (JP)

(73) Assignee: NGK INSULATORS, LTD., Nagoya (JP)

( * ) Notice: Subject to any disclaimer, the term of this patent is extended or adjusted under 35 U.S.C. 154(b) by 24 days.

(21) Appl. No.: 14/225,537

(22) Filed: Mar. 26, 2014

(65) Prior Publication Data

US 2014/0295715 A1    Oct. 2, 2014

(30) Foreign Application Priority Data

Mar. 29, 2013  (JP) .................. 2013-073710

(51) Int. Cl.
 *H01R 13/428*  (2006.01)
 *H01R 13/424*  (2006.01)
 *G01N 27/406*  (2006.01)

(52) U.S. Cl.
 CPC .......... *H01R 13/424* (2013.01); *G01N 27/4062* (2013.01); *Y10T 29/49002* (2015.01)

(58) Field of Classification Search
 CPC .. H01R 13/424; H01R 13/432; H01R 12/592; H01R 13/5205; Y10T 29/49002; G01N 27/407; G01N 27/4077
 USPC ..................... 439/744, 660, 607.41
 See application file for complete search history.

(56) References Cited

U.S. PATENT DOCUMENTS

| 5,711,863 | A | * | 1/1998 | Henkelmann et al. | ......... 204/428 |
| 6,231,348 | B1 | * | 5/2001 | Mayer et al. | .................... 439/33 |
| 7,340,942 | B2 | * | 3/2008 | Matsuo et al. | ............... 73/31.05 |
| 7,399,925 | B2 | * | 7/2008 | Yamauchi | .................... 174/74 R |
| 7,424,819 | B2 | * | 9/2008 | Fujita et al. | ................ 73/31.05 |
| 7,461,538 | B2 | * | 12/2008 | Matsuo et al. | ............... 73/23.31 |
| 7,563,118 | B1 | * | 7/2009 | McCauley et al. | ............ 439/260 |
| 8,047,051 | B2 | * | 11/2011 | McCauley et al. | ........... 73/23.31 |
| 8,579,634 | B2 | * | 11/2013 | Raquin et al. | .................... 439/31 |

(Continued)

FOREIGN PATENT DOCUMENTS

| EP | 2392920 A1 | 12/2011 |
| EP | 2500721 A1 | 9/2012 |
| JP | 5113941 B2 | 10/2012 |

OTHER PUBLICATIONS

An Extended European Search Report for the corresponding European patent application No. 14160906.5 issued on Oct. 28, 2014.

*Primary Examiner* — Jean F Duverne
(74) *Attorney, Agent, or Firm* — Global IP Counselors, LLP

(57) ABSTRACT

A contact fitting has a supporting portion capable of contacting a surface of a sensor element, and a conducting portion protruding in the same direction as the supporting portion and capable of contacting an electrode on the sensor element. Before the contact fitting is attached to the sensor element, a protrusion height of the conducting portion is 90% to 110% of a protrusion height of the supporting portion, and the protrusion heights and are relatively close to each other. The supporting portion and the conducting portion are elastically deformable and are curved in shape. The supporting portion and the conducting portion are arranged along a longitudinal direction of the contact fitting.

5 Claims, 5 Drawing Sheets

(56) References Cited

U.S. PATENT DOCUMENTS

| | | | |
|---|---|---|---|
| 8,636,532 B2* | 1/2014 | Masuda et al. | 439/263 |
| 8,677,804 B2* | 3/2014 | Masuda et al. | 73/31.05 |
| 9,003,867 B2* | 4/2015 | Kitoh | 73/31.05 |
| 2007/0141911 A1 | 6/2007 | Yoshikawa et al. | |
| 2011/0281472 A1 | 11/2011 | Masuda et al. | |

* cited by examiner

CONTACT MEMBER AND MANUFACTURING METHOD OF SENSOR

This application claims priority to Japanese Patent Application No. 2013-073710 filed on Mar. 29, 2013, the entirety of which is hereby incorporated by reference in its entirety.

BACKGROUND

1. Field of the Invention

The present invention relates to a contact member and a method for manufacturing a sensor.

2. Background Information

Contact members have been known, which are electrically connected, in a sensor such as a gas sensor, to electrodes on surfaces of a planar sensor element. For example, Japanese Patent No. 5113941 describes a long narrow contact member (contact fitting) made by bending a metal piece. The contact member has a supporting portion and a conducting portion protruding toward a sensor element. When the contact member is pressed toward the sensor element, the supporting portion contacts a surface of the sensor element and the conducting portion contacts an electrode. The conducting portion maintains an electrical connection between the sensor element and the contact member, and at the same time, the contact of the supporting portion with the sensor element prevents the sensor element from being broken by pressure from the conducting portion.

SUMMARY

When a contact member having two protruding portions, such as the conducting portion and the supporting portion in Japanese Patent No. 5113941, is brought into contact with a sensor element, a state of contact between an electrode and a protruding portion may vary among a plurality of contact members. If the state of contact between the electrode and the protruding portion varies, then variation in contact resistance may cause error in detecting electrical signals output from the sensor element through the contact members. Also, if the state of contact varies, there may be some contact members where contact between the electrode and the protruding portion is insufficient to fully maintain an electrical connection between them.

The present invention has been made to solve the problems described above. A primary object of the present invention is to reduce variation in the state of contact with an electrode on a sensor element among a plurality of contact members.

The present inventors focused on the fact that in contact members of related art, the protrusion heights of two protruding portions are not clearly defined and are different from each other, for example, one being 200 μm and the other being 300 μm. The present inventors then found out that variation in the state of contact between an electrode and a protruding portion can be reduced by adjusting the protrusion heights of two protruding portions, and completed the present invention.

A contact member according to the present invention is a contact member that can contact and be electrically connected to an electrode on a surface of a planar sensor element.

The contact member has a first protruding portion configured to be able to contact the surface of the sensor element, and a second protruding portion protruding in the same direction as the first protruding portion and configured to be able to contact the electrode.

A protrusion height of the second protruding portion is 90% to 110% of a protrusion height of the first protruding portion.

The contact member according to the present invention has the first protruding portion configured to be able to contact the surface of the sensor element, and the second protruding portion protruding in the same direction as the first protruding portion and configured to be able to contact the electrode on the sensor element. The protrusion height of the second protruding portion is 90% to 110% of the protrusion height of the first protruding portion, that is, these protrusion heights are relatively close to each other. With this configuration, when the contact member is pressed toward the sensor element such that the first protruding portion contacts the surface of the sensor element and the second protruding portion contacts the electrode on the sensor element, it is possible to reduce variation in the state of contact between the second protruding portion and the electrode among a plurality of contact members. This is probably because since the protrusion heights of the first protruding portion and the second protruding portion are relatively close to each other, unevenness in pressure applied from these protruding portions to the sensor element is reduced and this stabilizes the pressure applied from the second protruding portion to the electrode. It is only necessary that the first protruding portion be able to contact the surface of the sensor element. For example, the first protruding portion, as well as the second protruding portion, may be able to contact the electrode on the sensor element. Also, for example, the contact member may have one or more additional protruding portions configured to be able to contact the surface of the sensor element and protruding in the same direction as the first protruding portion and the second protruding portion. In other words, the contact member may have three or more protruding portions. In this case, if the protrusion height of one of the three or more protruding portions is selected as a reference height, the protrusion heights of the other protruding portions may be 90% to 110% of the reference height.

In the contact member according to the present invention, the first protruding portion and the second protruding portion may be equal in protrusion height. This makes it possible to more effectively reduce variation in the state of contact between the second protruding portion and the electrode among a plurality of contact members. Here, the phrase "equal in protrusion height" includes the cases where the protrusion heights are substantially equal, such as the cases of manufacturing error where there is a slight difference between the protrusion heights.

In the contact member according to the present invention, the first protruding portion and the second protruding portion may be elastically deformable. With this configuration, when the contact member is pressed toward the sensor element, the first protruding portion and the second protruding portion are elastically deformed. This makes it easier to maintain contact between the contact member and the sensor element.

In the contact member according to the present invention, the first protruding portion and the second protruding portion may be curved in shape. Thus, the first protruding portion and the second protruding portion can be relatively easily formed, for example, by bending.

In the contact member according to the present invention, the first protruding portion and the second protruding portion may be arranged along a longitudinal direction of the contact member. As compared to arranging the first protruding portion and the second protruding portion along the shorter sides of the contact member, arranging them along the longitudinal direction of the contact member is more prone to cause unevenness in pressure applied from the first protruding portion and the second protruding portion to the sensor element, and thus it is of great significance to apply the present invention.

A method for manufacturing a sensor according to the present invention includes the steps of:

(a) preparing a contact member having a first protruding portion and a second protruding portion protruding in the same direction, and a planar sensor element having an electrode on a surface thereof; and (b) sandwiching the sensor element and the contact member with a pressing member such that the first protruding portion contacts the surface of the sensor element and the second protruding portion contacts the electrode, and securing the pressing member while the contact member is being pressed against the sensor element by the pressing member, wherein in the contact member prepared in the step (a), a protrusion height of the second protruding portion is 90% to 110% of a protrusion height of the first protruding portion.

In the method for manufacturing a sensor according to the present invention, the pressing member sandwiches the sensor element and the contact member such that the first protruding portion of the contact member contacts the surface of the sensor element and the second protruding portion of the contact member contacts the electrode on the sensor element. Then, the pressing member is secured together, with the contact member pressed against the sensor element. Before the contact member is pressed, the protrusion height of the second protruding portion is 90% to 110% of the protrusion height of the first protruding portion, that is, the protrusion heights of the first and second protruding portions are relatively close to each other. Therefore, it is possible to reduce variation in the state of contact between the second protruding portion and the electrode among a plurality of sensors manufactured by the method including the steps described above. The sensors may be, for example, gas sensors configured to detect a concentration of a predetermined gas in gas under measurement. The "gas under measurement" may be, for example, car exhaust gas. The "concentration of a predetermined gas" may be, for example, NOx or oxygen concentration.

BRIEF DESCRIPTION OF THE DRAWINGS

Referring now to the attached drawings which form a part of this original disclosure:

FIG. 6 illustrates a positional relationship between contact fittings 71 and a sensor element 20 as viewed from a first housing 51a.

DETAILED DESCRIPTION OF EMBODIMENTS

Embodiments of the present invention will now be described with reference to the drawings.

Figure 1:
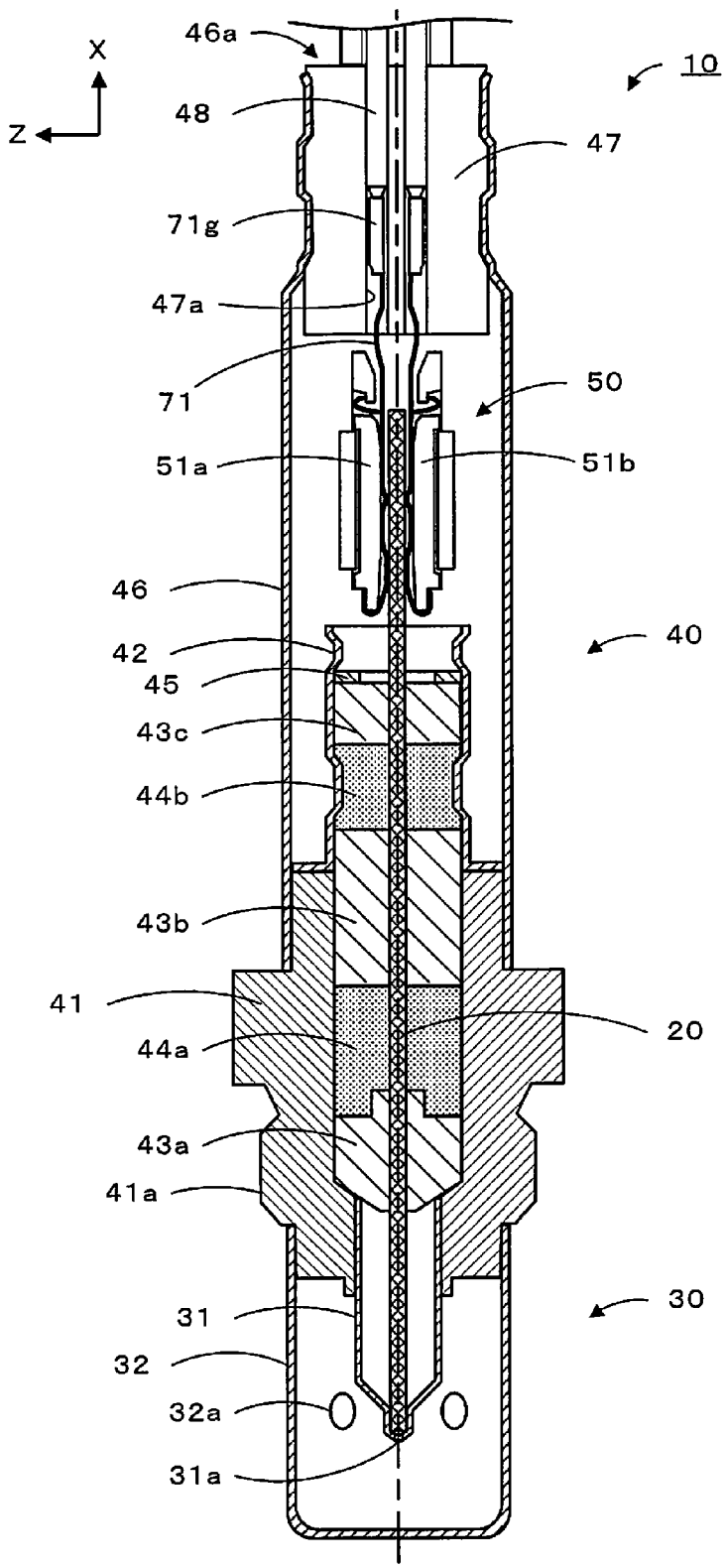
FIG. 1 is a longitudinal sectional view of a gas sensor 10 according to the present embodiment.
Figure 2:
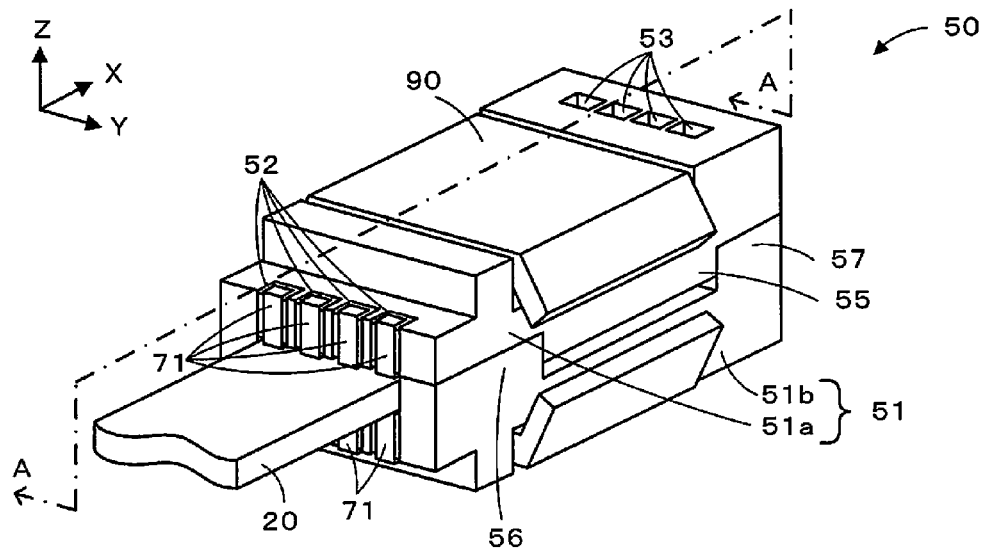
FIG. 2 is a perspective view of a connector 50.
Figure 3:
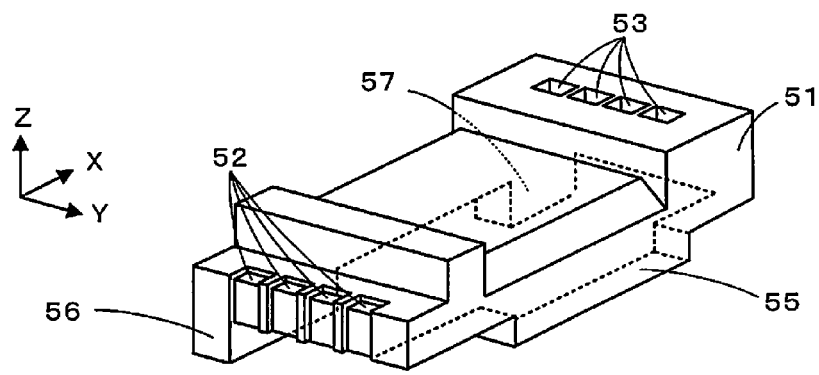
FIG. 3 is an exploded perspective view illustrating a housing 51 of the connector 50.
Figure 4:
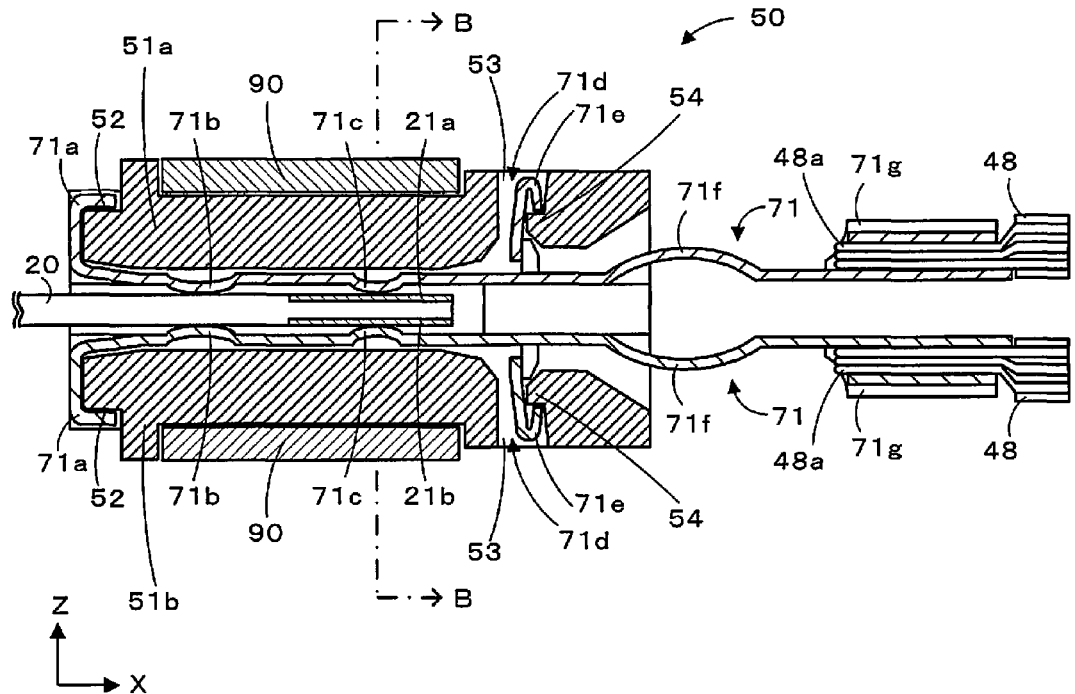
FIG. 4 is a cross-sectional view taken along line A-A of FIG. 2.
Figure 5:
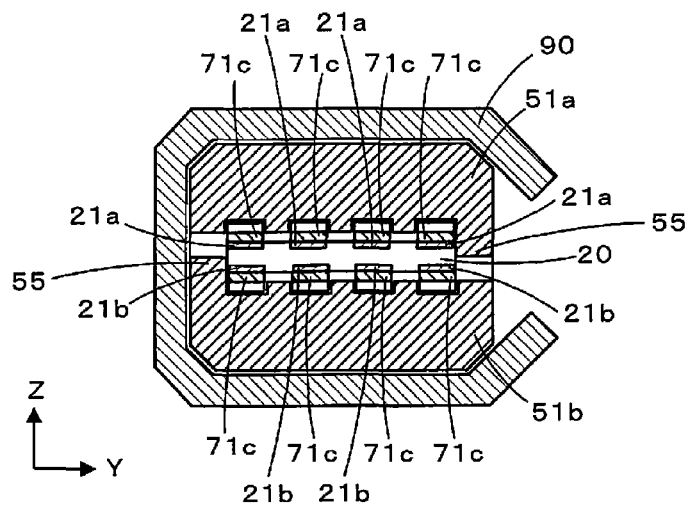
FIG. 5 is a cross-sectional view taken along line B-B of FIG. 4.
Figure 6:
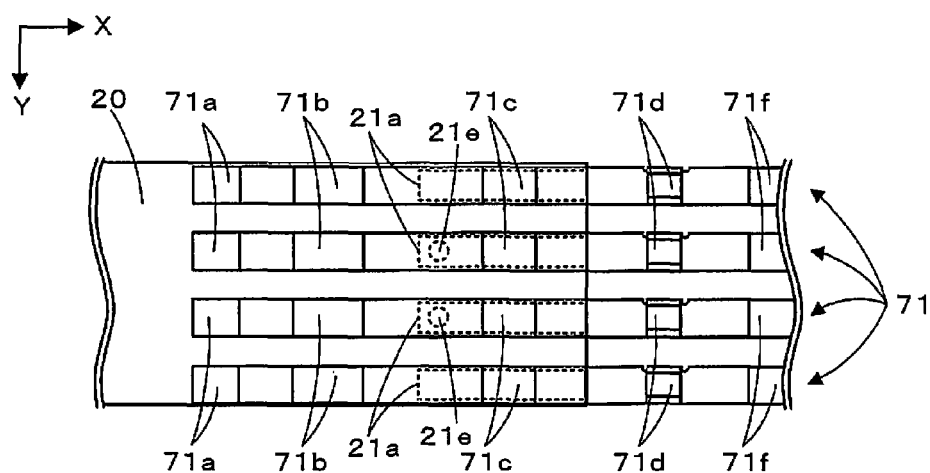

FIG. 1 is a longitudinal sectional view of a gas sensor 10 including contact fittings 71, each of which is an embodiment of a contact member according to the present invention. FIG. 2 is a perspective view of a connector 50. FIG. 3 is an exploded perspective view illustrating a housing 51 of the connector 50. FIG. 4 is a cross-sectional view taken along line A-A of FIG. 2. FIG. 5 is a cross-sectional view taken along line B-B of FIG. 4. FIG. 6 illustrates a positional relationship between contact fittings 71 and a sensor element 20 as viewed from a first housing 51a.

As illustrated in FIG. 1, the gas sensor 10 includes the sensor element 20 that measures a predetermined gas component in gas under measurement, a protective cover 30 that protects one end portion of the sensor element 20, and a sensor assembly 40 that includes the connector 50 electrically connected to the sensor element 20. For example, the gas sensor 10 is attached to an exhaust gas pipe of a vehicle and used to measure gas components, such as NOx and $O_2$, contained in exhaust gas, which is gas under measurement.

The sensor element 20 is a long narrow plate-like element. The sensor element 20 is formed by stacking, for example, six ceramic substrates composed of oxygen-ion conductive solid electrolyte layers, such as zirconia ($ZrO_2$) layers. One end portion of the sensor element 20 adjacent to the protective cover 30 is referred to as a tip end, and the other end portion of the sensor element 20 adjacent to the connector 50 is referred to as a base end. As illustrated in FIG. 5, four first-surface electrodes 21a are disposed on a first surface (upper surface in FIG. 5) of the base end of the sensor element 20, and four second-surface electrodes 21b are disposed on a second surface (lower surface in FIG. 5) of the base end of the sensor element 20. The first-surface electrodes 21a and the second-surface electrodes 21b are collectively referred to as electrodes 21. The electrodes 21 are for applying a voltage to the sensor element 20, and for deriving electromotive force or current produced in accordance with the concentration of a gas component detected by the sensor element 20. Although not shown, the electrodes 21 are electrically connected, through electrical paths inside the sensor element 20, to electrodes inside the tip end of the sensor element 20. The positions of the first-surface electrodes 21a and the second-surface electrodes 21b will be described later on.

As illustrated in FIG. 1, the protective cover 30 is disposed around the tip end of the sensor element 20. The protective cover 30 includes an inner protective cover 31 that covers the tip end of the sensor element 20, and an outer protective cover 32 that covers the inner protective cover 31. The inner protective cover 31 has a cylindrical shape and is provided with an inner protective cover hole 31a for introducing gas under measurement to the tip end of the sensor element 20. The outer protective cover 32 has a cylindrical shape with a bottom and is provided with outer protective cover holes 32a, in the periphery thereof, for introducing gas under measurement. The inner protective cover 31 and the outer protective cover 32 are made of metal, such as stainless steel.

The sensor assembly 40 includes a main fitting 41 made of metal, an inner cylinder 42 and an outer cylinder 46 having a cylindrical shape and secured by welding to the main fitting 41, and the connector 50 connected to the base end of the sensor element 20. The main fitting 41 can be attached, for example, to an exhaust gas pipe of a vehicle with an external thread 41a. The inner cylinder 42 contains a plurality of ceramic supporters 43a to 43c, and ceramic powders 44a and 44b, such as talcum powder, with which a space between the ceramic supporters 43a and 43b and a space between the ceramic supporters 43b and 43c are filled. The ceramic supporters 43a to 43c and the ceramic powders 44a and 44b are sealed in the space between a metal ring 45 and the inner wall of the main fitting 41. The inner cylinder 42, the sensor element 20, and the connector 50 are surrounded by the outer cylinder 46. Lead wires 48 connected to the connector 50 lead through an open end 46a to the outside of the outer cylinder 46. The lead wires 48 are electrically connected through the connector 50 to the respective electrodes 21 on the sensor element 20. A space between the outer cylinder 46 and the lead wires 48 is sealed with a rubber stopper 47.

The connector 50 will now be described in detail. As illustrated, the connector 50 includes the first housing 51a and a second housing 51b made of ceramic, such as sintered alumina; the contact fittings 71 held by the first housing 51a or the second housing 51b and facing, and in contact with, the respective electrodes 21 on the sensor element 20, and a metal clamp 90 configured to clamp the first housing 51a and the second housing 51b.

The first housing 51a and the second housing 51b are each configured to hold four contact fittings 71 arranged in a direction (Y direction) orthogonal to a longitudinal direction of the contact fittings 71 (X direction). The same components in the first housing 51a and the second housing 51b, which are of the same shape, are denoted by the same reference numerals. The first housing 51a and the second housing 51b are collectively referred to as the housings 51. Each housing 51 has four retaining grooves 52 for retaining the contact fittings 71, four insertion holes 53 for insertion of the contact fittings 71, and retainers 54 provided in the respective insertion holes 53 to retain the contact fittings 71. Each housing 51 has, in the Y direction, a protrusion 55 in one side thereof and regulating members 56 and 57 in the other side thereof, on both sides of the sensor element 20 (see FIGS. 2 and 3). The regulating members 56 and 57 are configured to regulate the distance between the first housing 51a and the second housing 51b in the Z direction. The protrusion 55 is configured to fit in an indentation between the regulating member 56 and the regulating member 57 of the opposite housing 51. This can fix the relative position of the first housing 51a and the second housing 51b in the X direction.

The contact fittings 71 are metal members held by the housings 51 in place, where they face the respective electrodes 21 on the sensor element 20. Each of the contact fittings 71 has a tip portion 71a curved and retained by the retaining groove 52, a supporting portion 71b curved and protruding toward the sensor element 20, a conducting portion 71c curved and protruding toward the sensor element 20 to contact the electrode 21, an upright portion 71d to be inserted into the insertion hole 53, a curved portion 71f leading to the outside of the connector 50, and a holding portion 71g crimped to hold a plurality of cores 48a of the lead wires 48 outside the connector 50. The supporting portion 71b and the conducting portion 71c are arranged along the longitudinal direction of the contact fitting 71 (in the X direction in FIG. 4), and the conducting portion 71c is closer to the holding portion 71g than the supporting portion 71b is. Both the supporting portion 71b and the conducting portion 71c are elastically deformable, and their spring constants are, for example, in the range of 500 N/mm to 4000 N/mm. The upright portion 71d has a hook 71e having a curved shape and retained by the retainer 54. The conducting portions 71c of the contact fittings 71 held by the first housing 51a are configured to face and contact the respective first-surface electrodes 21a on the sensor element 20, and the conducting portions 71c of the contact fittings 71 held by the second housing 51b are configured to face and contact the respective second-surface electrodes 21b on the sensor element 20 (see FIGS. 4 and 5).

The positional relationship between the contact fittings 71 and the electrodes 21 on the sensor element 20 will now be described. As illustrated in FIGS. 4 and 6, the first-surface electrodes 21a on the sensor element 20 extend from the base end of the sensor element 20 to a position between the conducting portions 71c and the supporting portions 71b. Of the four first-surface electrodes 21a arranged in the Y direction, two first-surface electrodes 21a in the center are electrically connected to respective through holes 21e provided for electrical connection to the electrical paths inside the sensor element 20. As illustrated in FIG. 6, each of the through holes 21e is at a position between the conducting portion 71c and the supporting portion 71b. Note that the positional relationship between the second-surface electrodes 21b and the contact fittings 71, and the positions of through holes 21e electrically connected to the second-surface electrodes 21b are the same as this, and thus will not be described here.

As illustrated in FIGS. 2 and 5, the clamp 90 is formed by bending a metal plate. The clamp 90 has an elastic force with which the first housing 51a and the second housing 51b can be clamped and pressed in directions toward each other. When the first housing 51a and the second housing 51b are clamped with the elastic force, the regulating members 56 and 57 of the first housing 51a contact the second housing 51b, and the regulating members 56 and 57 of the second housing 51b contact the first housing 51a. This fixes the distance between the first housing 51a and the second housing 51b. When the clamp 90 clamps the first housing 51a and the second housing 51b, with the sensor element 20 and the contact fittings 71 sandwiched between the first housing 51a and the second housing 51b, such that the conducting portions 71c of the contact fittings 71 face the first-surface electrodes 21a or the second-surface electrodes 21b on the sensor element 20, the pressure from the clamp 90 elastically deforms the supporting portions 71b and the conducting portions 71c, which then clamp and secure the sensor element 20 in place. Since the supporting portions 71b and the conducting portions 71c are elastically deformed, the sensor element 20 can be reliably clamped and secured by the resulting pressure. Since the conducting portions 71c are elastically deformed, the electrical contact between the conducting portions 71c and the electrodes 21 can be reliably maintained.

Figure 7:
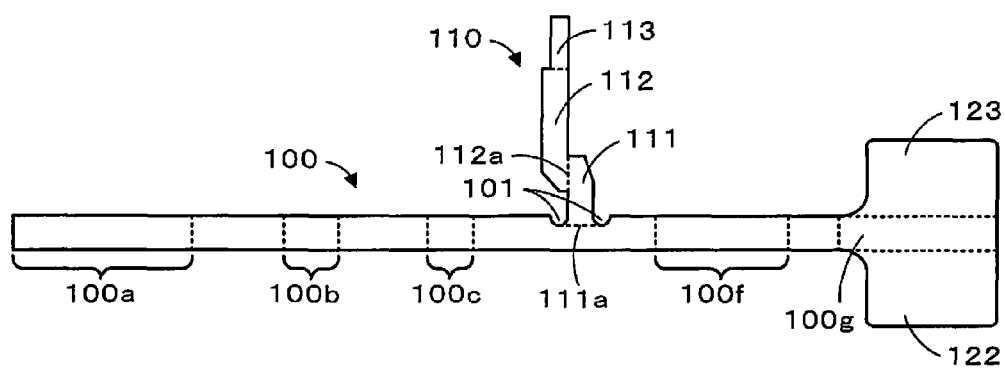
FIG. 7 illustrates a contact fitting 71 before bending.
Figure 8:
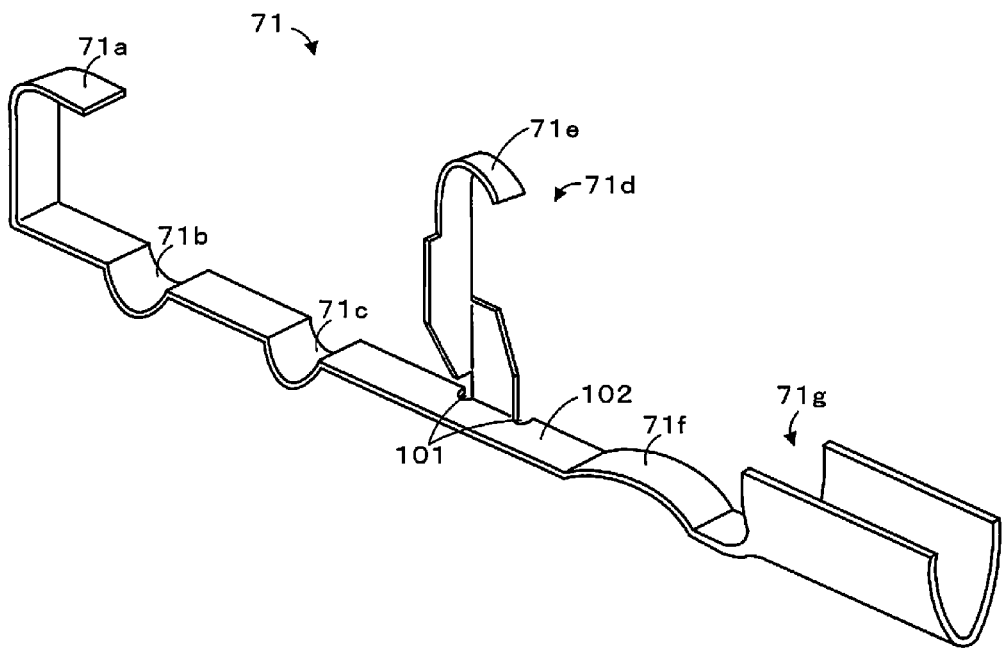
FIG. 8 is a perspective view of the contact fitting 71 after bending.
Figure 9:
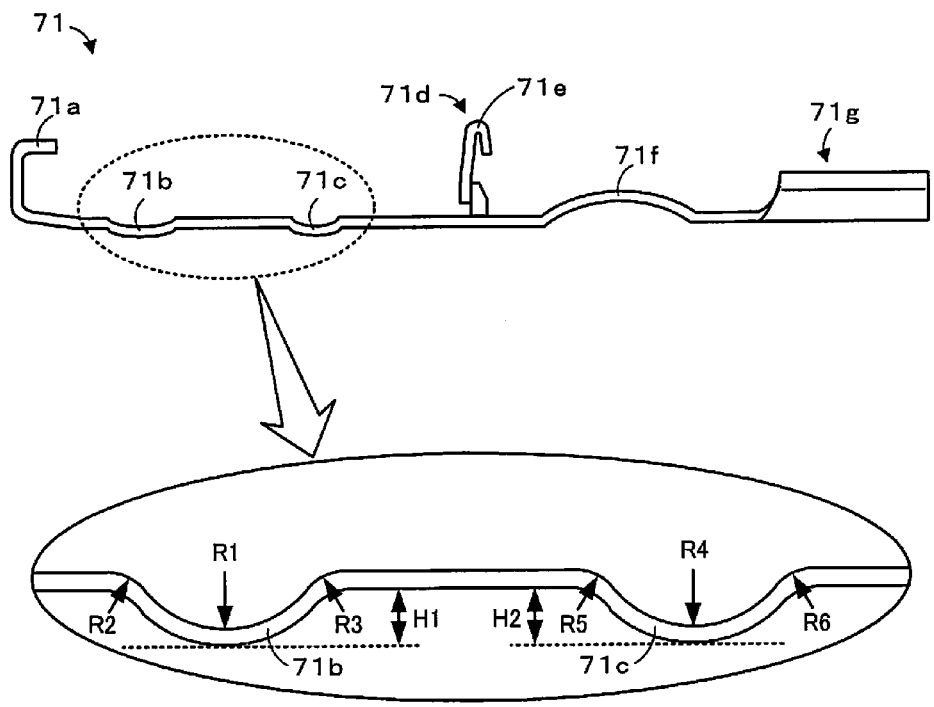
FIG. 9 is a side view of the contact fitting 71 after bending.

A method for manufacturing the contact fittings 71 will now be described. The contact fittings 71 are formed by die-cutting and bending a metal plate. FIG. 7 illustrates a contact fitting 71 before bending. FIG. 8 is a perspective view of the contact fitting 71 after bending. FIG. 9 is a side view of the contact fitting 71 after bending. As illustrated in FIG. 7, a metal plate is die-cut into a shape having a metal plate portion 100 of substantially rectangular shape, a metal piece 110 continuous with one of long sides of the metal plate portion 100, and substantially rectangular metal pieces 122 and 123 continuous with respective long sides of a region 100g at an end of the metal plate portion 100. The metal piece 122 is located across the region 100g from the metal piece 123. The tip portion 71a and the curved portion 71f illustrated in FIG. 4 are formed by bending a region 100a and a region 100f, respectively, of the metal plate portion 100 upward from the horizontal plane of FIG. 7. Also, the supporting portion 71b and the conducting portion 71c illustrated in FIG. 4 are formed by bending a region 100b and a region 100c, respectively, of the metal plate portion 100 downward from the horizontal plane of FIG. 7. The curved shapes of the supporting portion 71b and the conducting portion 71c are adjusted, as illustrated in FIG. 9, such that a protrusion height H2 of the conducting portion 71c is 90% to 110% of a protrusion height H1 of the supporting portion 71b. The hook 71e is formed by folding a region 111 along a straight line 111a upward from the horizontal plane of FIG. 7 until the region 111 is parallel with a direction perpendicular to the horizontal plane of FIG. 7, folding a region 112 along a straight line 112a toward the inside of the metal plate portion 100, and bending a region 113 along the longitudinal direction of the metal plate portion 100 toward the curved portion 71f. Thus, the metal piece 110 is bent into the upright portion 71d. As illustrated in FIGS. 7 and 8, the metal plate portion 100 has cutouts 101 with a depth greater than or equal to the thickness of the region 111. Thus, when the region 111 is folded along the straight line 111a, the region 111 is accommodated within a space directly above a front surface 102 (see FIG. 8) of the metal plate portion 100. The holding portion 71g is formed by raising the metal pieces 122 and 123 from the horizontal plane of FIG. 7. Thus, by bending a metal plate as described above, the contact fitting 71 having a three-dimensional shape illustrated in FIGS. 8 and 9 can be easily manufactured.

The shapes of the supporting portion 71b and the conducting portion 71c of the contact fitting 71 after bending and before attachment to the sensor element 20 will be described in detail. As illustrated in FIG. 9, the supporting portion 71b has a curved shape and protrudes by the protrusion height H1 in the direction opposite the tip portion 71a (downward in FIG. 9). The conducting portion 71c has a curved shape and protrudes by the protrusion height H2 in the direction opposite the tip portion 71a (downward in FIG. 9). As described above, the conducting portion 71c is formed such that the protrusion height H2 is 90% to 110% of the protrusion height H1. The closer the protrusion height H1 and the protrusion height H2, the better, and preferably the protrusion height H1 and the protrusion height H2 are equal. The phrase "the protrusion height H1 and the protrusion height H2 are equal" includes the cases where the protrusion heights are substantially equal, such as the cases of manufacturing error where there is a slight difference between them. The protrusion heights H1 and H2 are not limited to specific values but may range, for example, from 0.1 mm to 1 mm. A curvature radius R1 of the inner periphery (upper surface in FIG. 9) of the end of the protruding shape of the supporting portion 71b is, for example, 0.8 mm to 1.6 mm, and curvature radii R2 and R3 of the outer peripheries (upper surfaces in FIG. 9) of curved portions at both shoulders of the protruding shape of the supporting portion 71b are, for example, 1.2 mm to 2.2 mm. A curvature radius R4 of the inner periphery (upper surface in FIG. 9) of the end of the protruding shape of the conducting portion 71c is, for example, 0.8 mm to 1.6 mm, and curvature radii R5 and R6 of the outer peripheries (upper surfaces in FIG. 9) of curved portions at both shoulders of the protruding shape of the conducting portion 71c are, for example, 1.2 mm to 1.5 mm. The curvature radii R2 and R3 may be equal, and the curvature radii R5 and R6 may be equal. The curvature radii R5 and R6 may be either equal to or greater than the curvature radii R2 and R3.

Next, a method for manufacturing the gas sensor 10 including the contact fittings 71 after bending (see FIGS. 8 and 9) will be described. First, the main fitting 41 and the inner cylinder 42 are assembled, by welding, to be coaxial with each other. Then, the ceramic supporter 43a, the ceramic powder 44a, the ceramic supporter 43b, the ceramic powder 44b, and the ceramic supporter 43c are charged, into the main fitting 41 and the inner cylinder 42, such that they are arranged in this order from the side of the main fitting 41. This is followed by insertion of the metal ring 45. Next, the sensor element 20 is prepared and passed through the ceramic supporter 43c, the ceramic powder 44b, the ceramic supporter 43b, the ceramic powder 44a, and the ceramic supporter 43a in this order from the side of the metal ring 45. The ceramic supporters 43a to 43c, the ceramic powders 44a and 44b, and the metal ring 45 have a hole which is formed in advance and which allows the sensor element 20 to pass through. Next, the ceramic powders 44a and 44b are compressed by pressing the metal ring 45 and the main fitting 41 in directions toward each other. With the ceramic powders 44a and 44b compressed, the inner cylinder 42 outside the metal ring 45 is radially swaged at a position above the metal ring 45 in FIG. 1. Additionally, the inner cylinder 42 is radially swaged at a position where the ceramic powder 44b is located. A primary product composed of the main fitting 41 and the sensor element 20 is thus obtained.

After the primary product is obtained, the inner protective cover 31 and the outer protective cover 32 are attached by welding to the main fitting 41 to form the protective cover 30. At the same time, the outer cylinder 46 is attached by welding to the main fitting 41. Next, a plurality of (eight in the present embodiment) contact fittings 71 after bending (see FIGS. 8 and 9) are prepared. A plurality of (eight in the present embodiment) lead wires 48 and the rubber stopper 47 having through holes 47a are also prepared. After the plurality of lead wires 48 are drawn through the through holes 47a of the rubber stopper 47, the holding portions 71g of the contact fittings 71 are crimped around the respective cores 48a of the lead wires 48 to electrically connect the contact fittings 71 to the lead wires 48. The crimping is performed for each of the eight contact fittings 71 and the eight lead wires 48. This produces eight crimp bodies in which the contact fittings 71 are connected to the respective lead wires 48. Then, the housings 51 (the first housing 51a and the second housing 51b) and the clamp 90 are prepared. With four contact fittings 71 held each by the first housing 51a and the second housing 51b, the sensor element 20 is sandwiched between the first housing 51a and the second housing 51b. Thus, the sensor element 20 and the contact fittings 71 are sandwiched between the first housing 51a and the second housing 51b. In each of the contact fittings 71, as described with reference to FIGS. 4 to 6, the supporting portion 71b contacts the surface of the sensor element 20 and the conducting portion 71c contacts the electrode 21. In this state, the clamp 90 clamps the first housing 51a and the second housing 51b. Thus, the clamp 90 presses the first housing 51a and the second housing 51b in directions toward each other. By this pressure, the contact fittings 71 are pressed toward the sensor element 20, the supporting portions 71b are brought into contact with the surface of the sensor element 20, the conducting portions 71c are brought into contact with and electrically connected to the electrodes 21 on the sensor element 20, and the supporting portions 71b and the conducting portions 71c are elastically deformed to press the sensor element 20. Then, the rubber stopper 47 is inserted from the open end 46a into the outer cylinder 46, the outer cylinder 46 and the rubber stopper 47 are radially swaged, and the rubber stopper 47 is secured to the outer cylinder 46. When the outer cylinder 46 and the rubber stopper 47 are radially swaged, the resulting force may press the contact fittings 71 against the sensor element 20. Therefore, as an elastic force (pressure) of the clamp 90 increases, or as the diameter of the outer cylinder 46 and the rubber stopper 47 decreases by swaging, the pressure with which the supporting portions 71b and the conducting portions 71c press the sensor element 20 tends to increase. The gas sensor 10 is thus manufactured by the process described above.

Correspondences between components of the present embodiment and components of the present invention will be described. The sensor element 20 of the present embodiment corresponds to a sensor element of the present invention. The electrodes 21 (the first-surface electrodes 21a and the second-surface electrodes 21b) of the present embodiment corresponds to electrodes of the present invention. Each contact fitting 71 of the present embodiment corresponds to a contact member of the present invention. Each supporting portion 71b of the present embodiment corresponds to a first protruding portion of the present invention, and each conducting portion 71c of the present embodiment corresponds to a second protruding portion of the present invention. The housings 51 (the first housing 51a and the second housing 51b) of the present embodiment correspond to pressing members of the present invention.

According to the embodiments described in detail, the contact fittings 71 have each the supporting portion 71b that can contact the corresponding surface of the sensor element 20, and the conducting portion 71c that protrudes in the same direction as the supporting portion 71b and can contact the corresponding electrode 21 on the sensor element 20. Before the contact fitting 71 is attached to the sensor element 20 (see FIGS. 8 and 9), the protrusion height H2 of the conducting portion 71c is 90% to 110% of the protrusion height H1 of the supporting portion 71b, and the protrusion heights H1 and H2 are relatively close to each other. Thus, when the contact fitting 71 is pressed toward the sensor element 20 such that the supporting portion 71b contacts the surface of the sensor element 20 and the conducting portion 71c contacts the electrode 21 on the sensor element 20 (see FIGS. 4 to 6), it is possible to reduce variation in the state of contact between the conducting portion 71c and the electrode 21 among the plurality of contact fittings 71. Hence, for example, when a plurality of gas sensors 10 are manufactured, it is possible to reduce variation in the state of contact between the conducting portion 71c and the electrode 21 among the plurality of gas sensors 10. This is probably because since the protrusion heights H1 and H2 of the supporting portion 71b and the conducting portion 71c are relatively close to each other, unevenness in pressure applied from the supporting portion 71b and the conducting portion 71c to the sensor element 20 is reduced and this stabilizes the pressure applied from the conducting portion 71c to the electrode 21. If the state of contact between the electrode 21 and the conducting portion 71c varies, then variation in contact resistance between the electrode 21 and the conducting portion 71c may cause error in detecting electrical signals output from the sensor element 20 through the contact fittings 71. Also, if the state of contact varies, there may be some contact fittings 71 where contact between the electrode 21 and the conducting portion 71c is insufficient to fully maintain an electrical connection between them. This can be reduced by reducing variation in the state of contact between the electrode 21 and the conducting portion 71c.

By making the protrusion heights H1 and H2 of the supporting portion 71b and the conducting portion 71c equal, it is possible to more effectively reduce variation in the state of contact between the conducting portion 71c and the electrode 21 among the plurality of contact fittings 71.

The supporting portion 71b and the conducting portion 71c are configured to be elastically deformable as described above. Therefore, when the contact fitting 71 is pressed toward the sensor element 20, the supporting portion 71b and the conducting portion 71c are elastically deformed. This makes it easier to maintain contact between the contact fitting 71 and the sensor element 20.

Since the supporting portion 71b and the conducting portion 71c are curved in shape, they can be relatively easily formed, for example, by bending.

The supporting portion 71b and the conducting portion 71c are arranged along the longitudinal direction of the contact fitting 71. As compared to arranging the supporting portion 71b and the conducting portion 71c along the shorter sides of the contact fitting 71, arranging them along the longitudinal direction is more prone to cause unevenness in pressure applied from the supporting portion 71b and the conducting portion 71c to the sensor element 20, and thus it is of great significance to apply the present invention.

The method for manufacturing the gas sensor 10 includes the step of preparing the contact fittings 71 and the sensor element 20; and the step of sandwiching the sensor element 20 and the contact fittings 71 between the housings 51 such that the supporting portions 71b each contacts the corresponding surface of the sensor element 20 and the conducting portions 71c each contacts the corresponding electrode 21, and securing the housings 51 while the contact fittings 71 are being pressed against the sensor element 20 by the housings 51. Before the contact fittings 71 are pressed, the protrusion height H2 of the conducting portion 71c is 90% to 110% of the protrusion height H1 of the supporting portion 71b, that is, the protrusion heights H1 and H2 are relatively close to each other. Therefore, it is possible to reduce variation in the state of contact between the conducting portion 71c and the electrode 21 among a plurality of gas sensors 10 manufactured by the method including the steps described above.

It is obvious that the present invention is not limited to the embodiments described above, and may be implemented in various forms within the technical scope of the present invention.

For example, although the supporting portion 71b of each contact fitting 71 does not contact the electrode 21 on the sensor element 20 in the embodiments described above, the supporting portion 71b may be able to contact the electrode 21 as long as it can contact the surface of the sensor element 20.

Although the supporting portion 71b and the conducting portion 71c of each contact fitting 71 are curved in shape in the embodiments described above, they may be of other shapes, as long as they protrude in the same direction and the protrusion height H2 is 90% to 110% of the protrusion height H1.

Although the supporting portion 71b and the conducting portion 71c of each contact fitting 71 are elastically deformable in the embodiments described above, the present invention is not limited to this. Even when the supporting portion 71b and the conducting portion 71c are not elastically deformable, the contact between the conducting portion 71c and the electrode 21 can be maintained, for example, by pressing the contact fittings 71 toward the sensor element 20 with the housings 51 or the clamp 90.

In the embodiments described above, the protrusion height H2 is 90% to 110% of the protrusion height H1 before the contact fitting 71 is attached to the sensor element 20 (see FIGS. 8 and 9). Even in the state where the contact fitting 71 is attached to the sensor element 20 (see FIGS. 4 to 6), the protrusion height H2 may still be 90% to 110% of the protrusion height H1. However, since the contact fitting 71 is elastically deformed when attached to the sensor element 20, the protrusion height H2 does not necessarily need to be 90% to 110% of the protrusion height H1 in this state. Similarly, the protrusion height H2 may be 90% to 110% of the protrusion height H1 not only in the state before the contact fitting 71 is attached to the sensor element 20, but even in the state after the contact fitting 71 is attached to the sensor element 20 (e.g., after the gas sensor 10 is manufactured) and the connector 50 is disassembled to take out the contact fitting 71. However, because the contact fitting 71 may be plastically deformed, for example, by an elastic force of the clamp 90, pressure generated by swaging the outer cylinder 46 and the rubber stopper 47, or vibration during use of the gas sensor 10, the protrusion height H2 does not necessarily need to be 90% to 110% of the protrusion height H1 in the state after the connector 50 is disassembled and the contact fitting 71 is taken out.

In the embodiments described above, each contact fitting 71 has two protruding portions, the supporting portion 71*b* and the conducting portion 71*c*, as protruding portions that can contact the sensor element 20. Alternatively, the contact fitting 71 may have three or more protruding portions that can contact the sensor element 20. In this case, if the protrusion height of one of the three or more protruding portions is selected as a reference height, the protrusion heights of all the other protruding portions may be 90% to 110% of the reference height.

EXAMPLES

Example 1

As Example 1, the contact fitting 71 illustrated in FIGS. 8 and 9 was prepared by the manufacturing method described above. The contact fitting 71 of Example 1 is 0.7 mm wide, 0.2 mm thick, and 22 mm long. The supporting portion 71*b* has a designed protrusion height H1 of 0.2 mm, a curvature radius R1 of 1.6 mm, a curvature radius R2 of 2.2 mm, and a curvature radius R3 of 2.2 mm. The conducting portion 71*c* has a designed protrusion height H2 of 0.2 mm, a curvature radius R4 of 0.8 mm, a curvature radius R5 of 1.2 mm, and a curvature radius R6 of 1.2 mm. The material of the contact fitting 71 is SUS304.

Comparative Example 1

A contact fitting of Comparative Example 1 was prepared to have the same shape as that of the contact fitting 71 of Example 1, except that the designed protrusion height H1 of the supporting portion 71*b* was 0.3 mm.

Example 2

A contact fitting of Example 2 was prepared to have the same shape as that of the contact fitting 71 of Example 1, except that the designed protrusion height H1 of the supporting portion 71*b* was 0.21 mm.

Example 3

A contact fitting of Example 3 was prepared to have the same shape as that of the contact fitting 71 of Example 1, except that the designed protrusion height H1 of the supporting portion 71*b* was 0.19 mm.

Comparative Example 2

A contact fitting of Comparative Example 2 was prepared to have the same shape as that of the contact fitting 71 of Example 1, except that the designed protrusion height H1 of the supporting portion 71*b* was 0.25 mm.

Comparative Example 3

A contact fitting of Comparative Example 3 was prepared to have the same shape as that of the contact fitting 71 of Example 1, except that the designed protrusion height H1 of the supporting portion 71*b* was 0.17 mm.

Evaluation Test

Forty contact fittings 71 of Example 1 were prepared. For each of the 40 contact fittings 71 before being attached to the sensor element 20, the protrusion heights H1 and H2 were measured to derive a maximum value, a minimum value, an average value, a standard deviation a, an average value +5σ, and an average value −5σ of the protrusion heights H2. Additionally, 32 contact fittings 71 of Example 1 were prepared. By the manufacturing method described above, the 32 contact fittings 71 were attached to the corresponding sensor elements 20 to make the gas sensors 10. Then the connector 50 of each of the gas sensors 10 was disassembled to take out contact fittings 71. For each of the 32 contact fittings 71, the protrusion heights H1 and H2 were measured to derive a maximum value, a minimum value, an average value, a standard deviation a, an average value +5σ, and an average value −5σ of the protrusion heights H2. Similarly, for each of contact fittings of Comparative Example 1, Examples 2 to 3, and Comparative Examples 2 to 3 before being attached to the sensor elements 20 and after being taken out of manufactured gas sensors 10, the protrusion heights H1 and H2 were measured to derive a maximum value, a minimum value, an average value, a standard deviation a, an average value +5σ, and an average value −5σ of the protrusion heights H2. Note that 32 contact fittings of Comparative Example 1 were measured before being attached to the sensor elements 20, and 240 contact fittings of Comparative Example 1 were measured after the connectors 50 were disassembled and the contact fittings 71 were taken out. Similarly, 40 contact fittings of Example 2 were measured before attachment, and 32 contact fittings of Example 2 were measured after disassembling. Forty contact fittings of Example 3 were measured before attachment, and 32 contact fittings of Example 3 were measured after disassembling. Thirty-two contact fittings of Comparative Example 2 were measured before attachment, and 32 contact fittings of Comparative Example 2 were measured after disassembling. Thirty-two contact fittings of Comparative Example 3 were measured before attachment, and 32 contact fittings of Comparative Example 3 were measured after disassembling. Contact fittings having a standard deviation a within 15 μm after disassembling were rated as good.

Table 1 shows the designed protrusion heights H1 and H2 and the curvature radii R1 to R6 in the contact fittings of Example 1, Comparative Example 1, Examples 2 to 3, and Comparative Examples 2 to 3. Table 2 shows results of the evaluation test.

TABLE 1

| | | EXAMPLE 1 | COMPARATIVE EXAMPLE 1 | EXAMPLE 2 | EXAMPLE 3 | COMPARATIVE EXAMPLE 2 | COMPARATIVE EXAMPLE 3 |
|---|---|---|---|---|---|---|---|
| SUPPORTING PORTION | PROTRUSION HEIGHT H1 [mm] | 0.2 | 0.3 | 0.21 | 0.19 | 0.25 | 0.17 |
| | CURVATURE RADIUS R1 [mm] | 1.6 | 1.6 | 1.6 | 1.6 | 1.6 | 1.6 |
| | CURVATURE RADIUS R2 [mm] | 2.2 | 2.2 | 2.2 | 2.2 | 2.2 | 2.2 |

TABLE 1-continued

|  |  | EXAMPLE 1 | COMPARATIVE EXAMPLE 1 | EXAMPLE 2 | EXAMPLE 3 | COMPARATIVE EXAMPLE 2 | COMPARATIVE EXAMPLE 3 |
|---|---|---|---|---|---|---|---|
| CONDUCTING PORTION | CURVATURE RADIUS R3 [mm] | 2.2 | 2.2 | 2.2 | 2.2 | 2.2 | 2.2 |
|  | PROTRUSION HEIGHT H2 [mm] | 0.2 | 0.2 | 0.2 | 0.2 | 0.2 | 0.2 |
|  | CURVATURE RADIUS R4 [mm] | 0.8 | 0.8 | 0.8 | 0.8 | 0.8 | 0.8 |
|  | CURVATURE RADIUS R5 [mm] | 1.2 | 1.2 | 1.2 | 1.2 | 1.2 | 1.2 |
|  | CURVATURE RADIUS R6 [mm] | 1.2 | 1.2 | 1.2 | 1.2 | 1.2 | 1.2 |
|  | H2/H1 * 100 (%) | 100 | 66.6667 | 95.2381 | 105.263 | 80 | 117.647 |

TABLE 2

|  |  | EXAMPLE 1 | | COMPARATIVE EXAMPLE 1 | | EXAMPLE 2 | |
|---|---|---|---|---|---|---|---|
|  |  | BEFORE ATTACHMENT | AFTER DISASSEMBLING | BEFORE ATTACHMENT | AFTER DISASSEMBLING | BEFORE ATTACHMENT | AFTER DISASSEMBLING |
| PROTRUSION HEIGHT H2 | MAXIMUM VALUE [μm] | 201 | 177 | 199 | 196 | 200 | 177 |
|  | MINIUM VALUE [μm] | 185 | 133 | 188 | 93 | 190 | 133 |
|  | AVERAGE VALUE [μm] | 195 | 164 | 194 | 153 | 195 | 165 |
|  | STANDARD DEVIATION σ [μm] | 5 | 11 | 3 | 20 | 4 | 11 |
|  | AVERAGE VALUE + 5σ [μm] | 217 | 218 | 209 | 254 | 214 | 221 |
|  | AVERAGE VALUE − 5σ [μm] | 172 | 110 | 179 | 53 | 176 | 110 |
|  | RATE* | ○ | | X | | ○ | |

|  |  | EXAMPLE 3 | | COMPARATIVE EXAMPLE 2 | | COMPARATIVE EXAMPLE 3 | |
|---|---|---|---|---|---|---|---|
|  |  | BEFORE ATTACHMENT | AFTER DISASSEMBLING | BEFORE ATTACHMENT | AFTER DISASSEMBLING | BEFORE ATTACHMENT | AFTER DISASSEMBLING |
| PROTRUSION HEIGHT H2 | MAXIMUM VALUE [μm] | 201 | 182 | 200 | 192 | 199 | 188 |
|  | MINIUM VALUE [μm] | 184 | 132 | 188 | 132 | 188 | 128 |
|  | AVERAGE VALUE [μm] | 195 | 166 | 194 | 163 | 194 | 161 |
|  | STANDARD DEVIATION σ [μm] | 5 | 12 | 3 | 17 | 3 | 18 |
|  | AVERAGE VALUE + 5σ [μm] | 218 | 226 | 210 | 248 | 209 | 253 |
|  | AVERAGE VALUE − 5σ [μm] | 172 | 105 | 178 | 78 | 179 | 69 |
|  | RATE* | ○ | | X | | X | |

*EXAMPLE HAVING STANDARD DEVIATION σ [μm] WITHIN 15 WAS RATED AS GOOD.

As can be seen from Tables 1 and 2, the designed protrusion heights H1 and H2 are both 0.2 mm in Example 1. In Example 1, as can be seen from the result of the evaluation test before attachment, the measured protrusion heights H2 range from 185 μm to 201 μm, and are within the range of 90% to 110% of the measured protrusion heights H1 in all the contact fittings 71 prepared. On the other hand, in Comparative Example 1, the designed protrusion height H2 is about 66% of the designed protrusion height H1, and the measured protrusion heights H2 are not within the range of 90% to 110% of the measured protrusion heights H1. In Example 2, the designed protrusion height H2 is about 95% of the designed protrusion height H1. In Example 2, before attachment, the measured protrusion heights H2 range from 190 μm to 200 μm, and are within the range of 90% to 110% of the measured protrusion heights H1 in all the contact fittings 71 prepared. In Example 3, the designed protrusion height H2 is about 105% of the designed protrusion height H1. In Example 3, before attachment, the measured protrusion heights H2 range from 184 μm to 201 μm, and are within the range of 90% to 110% of the measured protrusion heights H1 in all the contact fittings 71 prepared. In Comparative Example 2, the designed protrusion height H2 is about 80% of the designed protrusion height H1. In Comparative Example 2, before attachment, the measured protrusion heights H2 are out of the range of 90% to 110% of the measured protrusion heights H1 in all the contact fittings 71 prepared.

In Comparative Example 3, the designed protrusion height H2 is about 118% of the designed protrusion height H1. In Comparative Example 3, before attachment, the measured protrusion heights H2 are out of the range of 90% to 110% of the measured protrusion heights H1 in all the contact fittings 71 prepared.

In the evaluation test after disassembling, the standard deviation σ of the protrusion heights H2 was 11 μm in Example 1, 20 μm in Comparative Example 1, 11 μm in Example 2, 12 μm in Example 3, 17 μm in Comparative Example 2, and 18 μm in Comparative Example 3. That is, the standard deviations σ of the protrusion heights H2 after disassembling in Examples 1 to 3 were smaller than those in Comparative Examples 1 to 3. Examples 1 to 3 had a standard deviation σ after disassembling of 15 μm or less and were rated as good, while Comparative Examples 1 to 3 were rated as poor. The protrusion heights H2 after disassembling differ from those before attachment, because the conducting portions 71c are plastically deformed by pressure with which the contact fittings are pressed against the sensor elements 20. Hence, a small standard deviation σ after disassembling means that variation in the degree of plastic deformation among a plurality of contact fittings is small. A small variation in the degree of plastic deformation among a plurality of contact fittings means that variation in pressure with which the contact fitting is pressed against the sensor element 20 among a plurality of contact fittings is small, or in other words, variation in the state of contact between the conducting portion 71c and the electrode 21 among a plurality of contact fittings is small. This shows that in Examples 1 to 3, where the protrusion height H2 are within the range of 90% to 110% of the protrusion heights H1, there is less variation in the state of contact between the conducting portion 71c and the electrode 21 when a contact fitting is pressed toward the sensor element 20 such that the supporting portion 71b contacts the surface of the sensor element 20 and the conducting portion 71c contacts the electrode 21.

The present application claims priority from Japanese Patent Application No. 2013-073710 filed on Mar. 29, 2013, the entire contents of which are incorporated herein by reference.

What is claimed is:

1. A contact member capable of contacting and being electrically connected to an electrode on a surface of a planar sensor element, the contact member comprising:
a first protruding portion configured to contact the surface of the sensor element, and protruding in a first direction; and
a second protruding portion protruding in the first direction and being configured to contact the electrode,
the second protrusion having a protrusion height 90% to 110% of a protrusion height of the first protruding portion,
the first and second protruding portions being formed by bending of a metal plate,
each of first and second protruding portions has a curved protruding shape having
a first portion having a concave surface on the side of metal plate facing away from the direction of protrusion of the protruding portion and providing an extremity of the protruding portion, and
two curved shoulders respectively on opposite sides of the extremity, each having a convex surface on the side of the metal plate facing away from the direction of protrusion of the protruding portion,
the concave surface of the first portion of the first protruding portion having a curvature radius of 0.8 mm to 1.6 mm,
the convex surfaces of the curved shoulders of the first protruding portion having curvature radii of 1.2 mm to 2.2 mm,
the concave surface of the first portion of the second protruding portion having a curvature radius of 0.8 mm to 1.6 mm,
the convex surfaces of the curved shoulders of the second protruding portion having curvature radii of 1.2 mm to 1.5 mm, and
the first and second protrusion portions having protrusion heights of 0.1 mm to 1 mm.

2. The contact member according to claim 1, wherein the protrusion height of the first protruding portion and the protrusion height of the second protruding portion being equal.

3. The contact member according to claim 1, wherein the first protruding portion and the second protruding portion are elastically deformable.

4. The contact member according to claim 1, wherein the first protruding portion and the second protruding portion are arranged along a longitudinal direction of the contact member.

5. A method for manufacturing a sensor, the method comprising:
preparing a contact member having a first protruding portion protruding in a first direction, a second protruding portion protruding in the first direction, and a planar sensor element having an electrode on a surface thereof,
the second protruding portion having a protrusion height 90% to 110% of a protrusion height of the first protruding portion,
the first and second protruding portions being formed by bending of a metal plate,
each of first and second protruding portions has a curved protruding shape having
a first portion having a concave surface on the side of metal plate facing away from the direction of protrusion of the protruding portion and providing an extremity of the protruding portion, and
two curved shoulders respectively on opposite sides of the extremity, each having a convex surface on the side of the metal plate facing away from the direction of protrusion of the protruding portion,
the concave surface of the first portion of the first protruding portion having a curvature radius of 0.8 mm to 1.6 mm, the convex surfaces of the curved shoulders of the first protruding portion having curvature radii of 1.2 mm to 2.2 mm,
the concave surface of the first portion of the second protruding portion having a curvature radius of 0.8 mm to 1.6 mm,
the convex surfaces of the curved shoulders of the second protruding portion having curvature radii of 1.2 mm to 1.5 mm, and
the first and second protrusion portions having protrusion heights of 0.1 mm to 1 mm; and sandwiching the sensor element and the contact member with a pressing member such that the first protruding portion contacts the surface of the sensor element and the second protruding portion contacts the electrode, and securing the pressing member while the contact member is being pressed against the sensor element by the pressing member.

* * * * *